US00PP12064P2

(12) United States Plant Patent
Ouding

(10) Patent No.: US PP12,064 P2
(45) Date of Patent: Aug. 21, 2001

(54) CHRYSANTHEMUM PLANT NAMED 'SUNNY YOROBIN'

(75) Inventor: Rick Ouding, Kalamazoo, MI (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/225,018

(22) Filed: Jan. 4, 1999

(51) Int. Cl.[7] ..... A01H 5/00
(52) U.S. Cl. ..... Plt./289
(58) Field of Search ..... Plt./289

(56) References Cited

U.S. PATENT DOCUMENTS

P.P. 6,404 * 11/1988 Mack et al. ..... Plt./289

P.P. 11,323 * 4/2000 Boeder ..... Plt./289

OTHER PUBLICATIONS

UPOU–ROM, 2000/02, Plant Variety Database, GTI Jouve Retrieval Software, citation for 'Sunny Yorobin'.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Sunny Yorobin', characterized by its uniformly mounded plant habit; relatively early flowering; decorative type inflorescences that are about 4.5 cm in diameter; attractive golden yellow ray and numerous inflorescences per plant.

1 Drawing Sheet

BACKGROUND OF THE INVENTION

The present invention relates to a new and distinct cultivar of Chrysanthemum plant, botanically known as *Dendranthema grandifora* and referred to by the cultivar name Sunny Yorobin.

The new Chrysanthemum is a naturally-occurring mutation of the *Dendranthema grandiflora* cultivar Robin, disclosed in U.S. Plant Pat. No. 8,300. The new Chrysanthemum was discovered by the Inventor as a single plant in a controlled environment in Kalamazoo, Mich., within a population of plants of 'Robin' in August, 1995. The selection of this plant was based on its unique ray floret color.

Asexual reproduction of the new cultivar by terminal cuttings taken in a controlled environment in Kalamazoo, Mich., and Salinas, Calif., has shown that the unique features of this new Chrysanthemum are stable and reproduced true to type in successive generations.

SUMMARY OF THE INVENTION

The cultivar Sunny Yorobin has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Yorobin'. These characteristics in combination distinguish 'Sunny Yorobin' as a new and distinct cultivar:

1. Uniformly mounded and dense plant habit.
2. Relatively early flowering.
3. Decorative type inflorescences that are about 4.5 cm in diameter.
4. Attractive golden yellow ray florets.
5. Numerous inflorescences per plant.

The new Chrysanthemum is similar to the parent cutivar Robin in plant habit. However plants of the new Chrysanthemum differ from plants of the cultivar Robin in ray floret color as ray florets of plants of the new Chrysanthemum are golden yellow and ray florets of plants of the cultivar Robin are orange bronze.

BRIEF DESCRIPTION OF THE PHOTOGRAPHS

The accompanying photographs illustrate the overall appearance of the new cultivar.

The photograph at the top of the sheet comprises a side perspective view of a typical flowering plant of 'Sunny Yorobin'.

The photograph at the bottom of the sheet comprises a close-up view of typical inflorescences of the cultivar 'Sunny Yorobin'. These photographs show the colors as true as it is reasonably possible to obtain in colored reproductions of this type. Floret and foliage colors in the photographs may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Leamington, Ontario, Canada, under conditions which approximate those generally used in commercial garden Chrysanthemum production. One rooted cutting was planted in a 15-cm container on Jul. 20, 1998 and plants were grown outdoors under natural season conditions. Measurements and numerical values represent averages for typical flowering containers.

Botanical classification: *Dendranthema grandiflora* cultivar 'Sunny Yorobin'.

Commercial classification: Decorative-type garden chrysanthemum.

Parentage: Naturally-occurring mutation of *Dendranthema grandiflora* cultivar Robin, disclosed in U.S. Plant Pat. No. 8,300.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous decorative-type garden Chrysanthemum. Inverted triangle. Stems initially upright, then outwardly spreading giving a uniformly mounded appearance to the plant. Freely branching with lateral branches potentially developing at every node, when pinched, about 6 laterals develop every node.

*Plant height.*—About 25 cm.

*Plant spread.*—About 36 cm.

*Foliage description.*—Leaf arrangement: Alternate. Length: About 4.8 cm. Width: About 3.7 cm. Apex: Mucronate. Base: Attenuate. Margin: Palmately lobed, sinuses parallel to divergent. Texture: Upper surface slightly pubescent; lower surface moderately pubescent. Veins prominent on lower surface. Petiole length: About 1.75 cm. Petiole diameter: About 3 mm. Color: Young foliage upper surface: 147A. Young foliage lower surface: Closet to 147B. Mature foliage upper surface: 147A. Mature foliage lower surface: 147B. Venation upper surface: 147B. Venation lower surface: 147B.

Inflorescence description:

*Appearance.*—Decorative-type inflorescence form with oblong-shaped ray florets. Inflorescences borne on terminals above foliage, arising from leaf axils. Disk and ray florets arranged acropetally on a capitulum. One inflorescence per terminal with numerous inflorescences per plant, about 9 per lateral stem.

*Flowering response.*—Under natural season conditions, plants flower in, mid-September in the Northern Hemisphere, about 66 days after planting, and flower for at least three weeks depending on weather conditions.

*Inflorescence bud (before showing color).*—Height: About 6 mm. Diameter: About 9 mm. Phyllary color: 143A.

*Inflorescence size.*—Diameter: About 4.5 cm. Depth (height): About 1.7 cm.

*Ray florets.*—Shape: Oblong, concave; short corolla tube. Length: About 2.1 cm. Width: About 8 mm. Apex: Rounded. Margin: Entire. Texture: Smooth, glabrous. Orientation: Initially upright, then horizontal. Number of ray florets per inflorescence: More than 225. Color: When opening: 12A. Opened inflorescence: Upper surface: 12A, fading to 12B. Lower surface: 12A to 12B.

*Disc florets.*—None observed.

*Peduncle.*—Aspect: Flexible, angled about 35° to the stem. Length: First peduncle: About 6.5 cm. Fourth peduncle: About 8.8 cm. Diameter: About 3 mm. Texture: Pubescent. Color: Close to 143A.

*Reproductive organs.*—Androecium: Not observed. Gynoecium: Present on ray florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Sunny Yorobin', as illustrated and described.

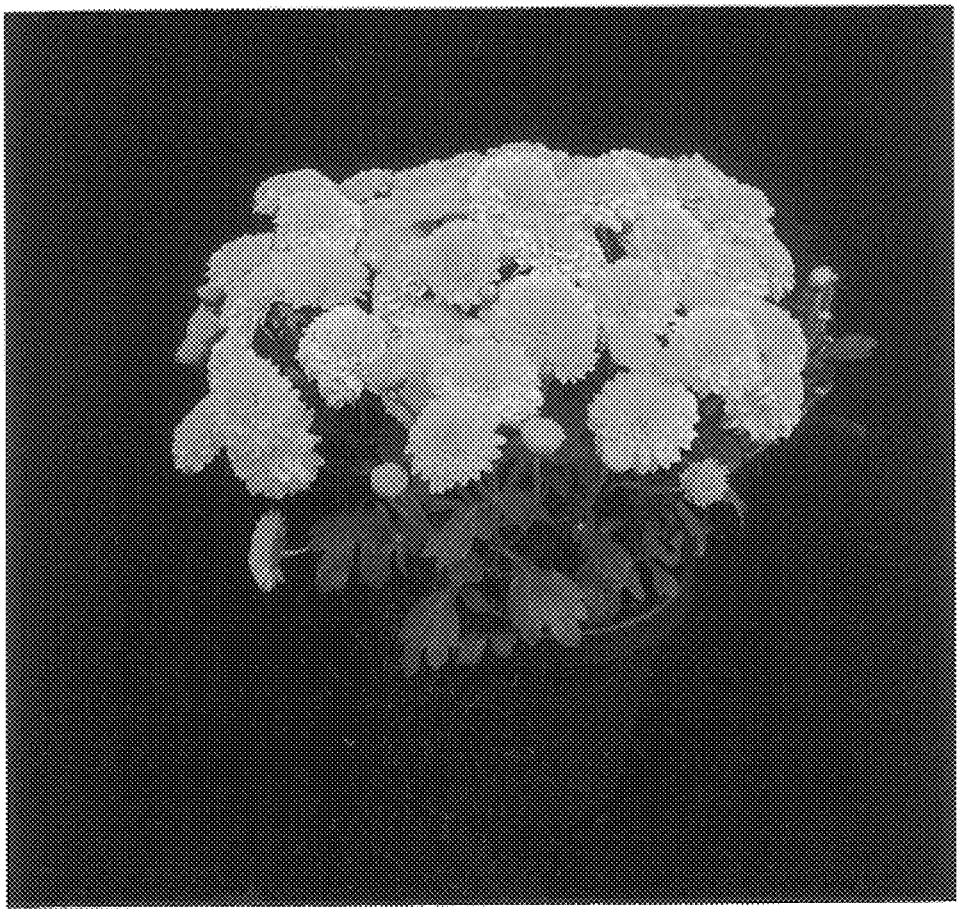
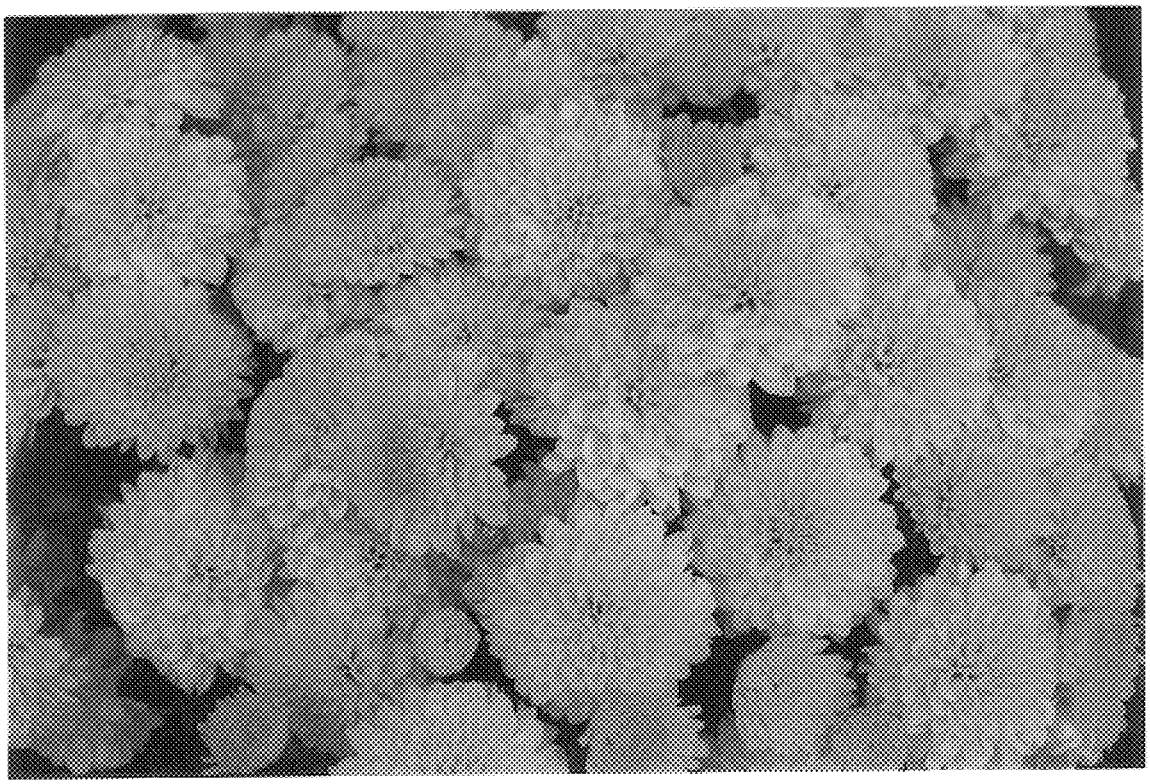

* * * * *